(12) United States Patent  
Kwon et al.

(10) Patent No.: US 9,136,551 B2
(45) Date of Patent: Sep. 15, 2015

(54) SULPHONATE BASED COMPOUND, POLYMER ELECTROLYTE MEMBRANE COMPRISING SAME AND FUEL CELL COMPRISING SAME

(71) Applicant: LG CHEM, LTD., Seoul (KR)

(72) Inventors: Hyejin Kwon, Seoul (KR); Seong Ho Choi, Daejeon (KR); Min-Jong Lee, Moscow (KR); Sergey Ulyakhin, Moscow (RU); Chong Kyu Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/111,399

(22) PCT Filed: Dec. 3, 2012

(86) PCT No.: PCT/KR2012/010385
§ 371 (c)(1),
(2) Date: Oct. 11, 2013

(87) PCT Pub. No.: WO2013/081437
PCT Pub. Date: Jun. 6, 2013

(65) Prior Publication Data
US 2014/0065512 A1 Mar. 6, 2014

(30) Foreign Application Priority Data
Dec. 2, 2011 (KR) .................. 10-2011-0128662

(51) Int. Cl.
*H01M 8/10* (2006.01)
*C07C 309/10* (2006.01)

(52) U.S. Cl.
CPC ........... *H01M 8/1039* (2013.01); *C07C 309/10* (2013.01); *H01M 8/1032* (2013.01); *H01M 8/1048* (2013.01); *H01M 8/1046* (2013.01); *Y02E 60/523* (2013.01)

(58) Field of Classification Search
CPC ............ H01M 8/1004; H01M 8/1023; H01M 8/1039; H01M 4/8605; H01M 2008/1095; H01M 2300/0082
See application file for complete search history.

(56) References Cited

U.S. PATENT DOCUMENTS 7,473,486 B2 * 1/2009 Yoshimura et al. ........... 429/484
2003/0013817 A1 1/2003 Lu
(Continued)

FOREIGN PATENT DOCUMENTS

JP            20087410 A     1/2008
KR   1020040107590 A    12/2004
(Continued)

OTHER PUBLICATIONS

Fabien Toulgoat et al., "An Efficient Preparations of New Sulfonyl Fluorides and Lithium Sulfonates", J. Org. Chem., 2007, 72 (24), pp. 9046-9052, See figure 1, See p. 9046.
(Continued)

*Primary Examiner* — Ula C Ruddock
*Assistant Examiner* — Thomas Parsons
(74) *Attorney, Agent, or Firm* — Dentons US LLP

(57) ABSTRACT

The present invention relates to a novel sulfonate-based compound, a method for preparing the same, a polymer electrolyte membrane comprising the sulfonate-based compound, a membrane electrode assembly comprising the same and a fuel cell comprising the same.

11 Claims, 3 Drawing Sheets

(56) References Cited

U.S. PATENT DOCUMENTS

| | | |
|---|---|---|
| 2006/0106190 A1 | 5/2006 | Balland-Longeau et al. |
| 2008/0114183 A1 | 5/2008 | Moore et al. |
| 2010/0167100 A1 | 7/2010 | Moore et al. |
| 2011/0112306 A1 | 5/2011 | Nagamori et al. |

FOREIGN PATENT DOCUMENTS

| | | |
|---|---|---|
| KR | 10-2010-0076902 A | 7/2010 |
| KR | 2011-0031236 A | 3/2011 |
| KR | 1020110031236 A | 3/2011 |

OTHER PUBLICATIONS

Kui Xu et al., "Highly Conductive Aromatic Ionomers with Perlfuorosulfonic Acid Side Chains for Elevated Temperature Fuel Cells", Macromolecules 2011, 44, 4605-4609 (Publication Date (Web): Jun. 7, 2011), pp. 4605-4609.

E. Paillard et al., "Electrochemical investigation of polymer electrolytes based on lithium 2-(phenylsulfanyl)-1,1,2,2-tetrafluoroethansulfonate", Electrochimica Acta, vol. 53, Issue 4, Dec. 31, 2007, pp. 1439-1443, See figure 1, pp. 1439-1443.

J. Org. Chem., vol. 72, pp. 9046-9052, 2007.

Macromolecules, vol. 44, pp. 4605-4609, Jul. 2011.

Macromolecules, vol. 42, No. 23, p. 9302-9306.

G.K.S. Prakash, et al.: "Preparation of α, α-difluoroalkanesulfonic acids", Journal of Fluorine Chemisty, vol. 125, No. 4, Apr. 2004, pp. 595-601, XP004507064.

M.N. Wadekar, et al.: "Synthesis of a Polymerizable Fluorosurfactant for the Construction of Stable Nanostructured Proton-Conducting Membranes", Journal of Organic Chemistry, vol. 75, No. 20, Sep. 16, 2010, pp. 6814-6819, XP055190783.

* cited by examiner

SULPHONATE BASED COMPOUND, POLYMER ELECTROLYTE MEMBRANE COMPRISING SAME AND FUEL CELL COMPRISING SAME

This application is a 35 USC §371 National Stage entry of International Application No. PCT/KR2012/010385, filed on Dec. 3, 2012, which claims priority of Korean Application No. 10-2011-0128662, filed on Dec. 2, 2011, all of which are hereby incorporated by reference in their entirety.

TECHNICAL FIELD

The present invention relates to a novel compound and a method for preparing the same. Specifically, the present invention relates to a sulfonate-based compound and a method for preparing the same.

Also, the present invention relates to a polymer electrolyte membrane and a fuel cell comprising the same. Specifically, the present invention relates to the polymer electrolyte membrane comprising a sulfonate-based compound and to a fuel cell comprising the same.

BACKGROUND ART

Recently, the development of various materials has been pursued in various technical fields. Also, the development of raw materials used in the development of the various materials has been pursued. For example, in the case of a polymer material, the polymer itself having desired properties has been developed by a process for polymerization of known monomers, the combination, compositional ratio or distribution state of monomers in the polymer, the steric structure or side-chain length of the polymer, the type of side chain, etc. In addition, the development of novel monomers used in the preparation of polymers has also been made.

Meanwhile, as the depletion of existing energy sources such as petroleum or coal has recently been predicted, alternative energy sources capable of replacing these energy sources have been of increasing interest. A fuel cell, which is one of such alternative energy sources, is receiving particular attention because of its advantages in that it has high efficiency, does not emit pollutants such as $NO_x$ and $SO_x$ and uses abundant fuel.

The fuel cell is a power generation system that converts energy, produced by a chemical reaction between a fuel and an oxidant into electrical energy. Typically, the fuel cell uses a hydrocarbon such as hydrogen, methanol or butane as a fuel and oxygen as an oxidant.

Fuel cells include a polymer electrolyte membrane fuel cell (PEMFC), a direct methanol fuel cell (DMFC), a phosphoric acid fuel cell (PAFC), an alkaline fuel cell (AFC), a molten carbonate fuel cell (MCFC), a solid oxide fuel cell (SOFC), and the like. Among them, the polymer electrolyte membrane fuel cell has high energy density and high output, and thus has been most actively studied. This polymer electrolyte membrane fuel cell has a difference from other fuel cells in that it does not use a liquid electrolyte but uses a solid polymer electrolyte membrane as an electrolyte.

DISCLOSURE

Technical Problem

The present invention provides a novel sulfonate-based compound and a method for preparing the same.

The present invention also provides a polymer electrolyte membrane and a fuel cell comprising the same.

Technical Solution

One embodiment of the present invention provides a compound represented by the following chemical formula 1:

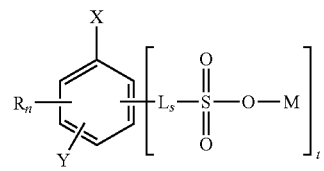

[Chemical formula 1]

wherein,

X, Y and R are each independently hydrogen, an aliphatic hydrocarbon group, an aromatic hydrocarbon group, a heterocyclic group, a reactive functional group or a group convertible into a reactive functional group; n is an integer ranging from 1 to 3, and when n is 2 or more, Rs may be the same as or different from each other and may together form an aliphatic or aromatic monocyclic or polycyclic ring;

L is a linking group containing at least one fluorine atom;

s is an integer ranging from 1 to 3, and when s is 2 or more, Ls are the same as or different from each other;

M is an element of Group 1 of the Periodic Table;

t is an integer ranging from 1 to 3, and when t is 2 or more, the substituents in the parenthesis are the same as or different from each other; and n+t is an integer ranging from 2 to 4.

Another embodiment of the present invention provides a method for preparing a compound of chemical formula 1, the method comprising the steps of:

a) preparing a compound of the following chemical formula 2:

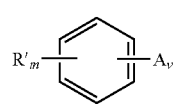

[Chemical formula 2]

wherein,

R's are the same as or different from each other and are each hydrogen, an aliphatic hydrocarbon group, an aromatic hydrocarbon group, a heterocyclic group, a reactive functional group or a group convertible into a reactive functional group; m is an integer ranging from 1 to 5, and when m is 2 or more, R's may be the same as or different from each other and may together form an aliphatic or aromatic monocyclic or polycyclic ring, A is a halogen group; v is an integer ranging from 1 to 3, and when v is 2 or more, As are the same as or different from each other, and m+v is an integer ranging from 2 to 6;

b) preparing a compound of the following chemical formula 3:

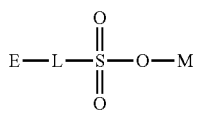
[Chemical formula 3]

wherein,
L and M are as defined in chemical formula 1, and
E is a halogen group; and
c) reacting the compound of chemical formula 2 with the compound of chemical formula 3 to obtain the compound of chemical formula 1.

The process for preparing the compound of chemical formula 1 may further comprise the step of d) converting at least one of the R' groups into a reactive functional group.

Another embodiment of the present invention provides a polymer electrolyte membrane comprising the compound of chemical formula 1.

Still another embodiment of the present invention provides a membrane electrode assembly comprising: an anode electrode; a cathode electrode; and a polymer electrolyte membrane interposed between the anode electrode and the cathode electrode and comprising the compound of chemical formula 1.

Yet another embodiment of the present embodiment provides a fuel cell comprising:

a stack comprising two or more membrane electrode assemblies according to the present invention and a separator interposed between the membrane electrode assemblies;

a fuel supply unit for supplying fuel to the stack; and an oxidant supply unit for supplying an oxidant to the stack.

Advantageous Effects

A compound according to the present invention is novel and has a very high possibility of being used as various materials or the raw materials thereof. For example, the compound according to the present invention can be used as a monomer for preparing a polymer.

In addition, the compound of chemical formula 1 described in the present specification is a monomer which can more efficiently cause phase separation of a hydrocarbon-based polymer, can be used for preparing a polymer as a raw material for a fuel cell polymer electrolyte membrane, and can be used as an additive in a fuel cell polymer electrolyte membrane. In particular, the compound of chemical formula 1 is suitable for use as the basic monomer of an electrolyte membrane wherein phase separation into hydrophilic and hydrophobic domains is important. Therefore, the polymer electrolyte membrane can be utilized as an ion exchange membrane of the fuel cell.

MODE FOR INVENTION

Figure 1:
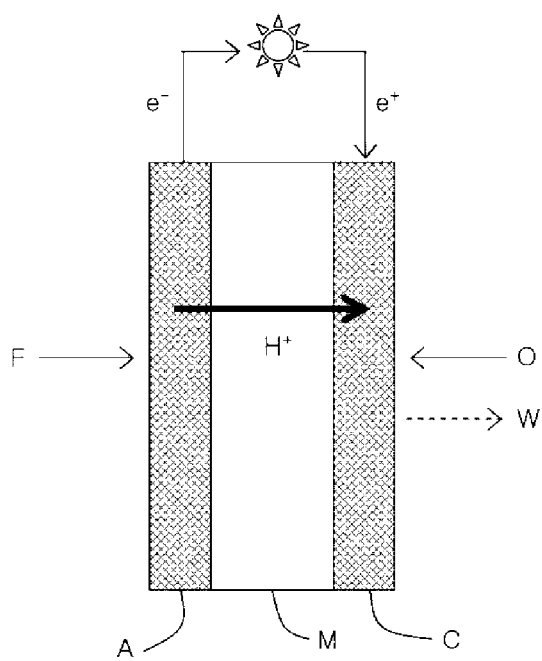
FIG. 1 is a schematic drawing showing the principle of electricity generation in a fuel cell.

Hereinafter, the present invention will be described in detail.

A compound according to one embodiment of the present invention has a structure represented by the following chemical formula 1:

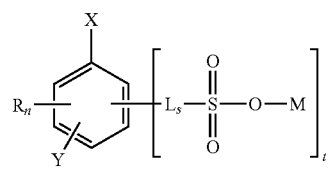
[Chemical formula 1]

wherein,
X, Y and R are each independently hydrogen, an aliphatic hydrocarbon group, an aromatic hydrocarbon group, a heterocyclic group, a reactive functional group or a group convertible into a reactive functional group; n is an integer ranging from 1 to 3, and when n is 2 or more, Rs may be the same as or different from each other and may together form an aliphatic or aromatic monocyclic or polycyclic ring;

L is a linking group containing at least one fluorine atom,
s is an integer ranging from 1 to 3, and when s is 2 or more, Ls are the same as or different from each other;

M is an element of Group 1 of the Periodic Table;
t is an integer ranging from 1 to 3, and when t is 2 or more, the substituents in the parenthesis are the same as or different from each other; and n+t is an integer ranging from 2 to 4.

In chemical formula 1, the bond between $SO_3$ and M is an ionic bond. The ionic bond is not active during the synthesis of the compound of chemical formula 1.

In the definitions of X, Y and R, the aliphatic hydrocarbon group is not specifically limited in carbon number. The aliphatic hydrocarbon group may have, for example, 1 to 20 carbon atoms. The aliphatic hydrocarbon group may contain a straight-chain, branched-chain, monocyclic or polycyclic moiety. Examples of the aliphatic hydrocarbon group include a straight or branched-chain alkyl group having 1 to 20 carbon atoms, a straight or branched-chain alkoxy group having 2 to 20 carbon atoms, a straight or branched-chain alkenyl group having 2 to 20 carbon atoms, an alkynyl group having 2 to 20 carbon atoms, a cycloalkyl group having 3 to 20 carbon atoms, a cycloalkenyl group having 3 to 20 carbon atoms, etc. In the present specification, it should be understood that, if a substituent bound to the benzene structure that is the core structure of chemical formula 1 is an aliphatic hydrocarbon, the aliphatic group may also be condensed or substituted with other substituents which are not aliphatic hydrocarbons.

In the definitions of X, Y and R, the aromatic hydrocarbon group is not specifically limited in carbon number. The aromatic hydrocarbon group may have, for example, 6 to 40 carbon atoms. The aromatic hydrocarbon group may comprise a monocyclic or polycyclic moiety. Examples of the aromatic hydrocarbon group include phenyl, naphthyl, antracenyl, pyrenyl, etc., which may additionally be substituted. In this specification, it should be understood that, if a substituent which is bound to the benzene ring that is the core structure of chemical formula 1 is an aromatic hydrocarbon, the aromatic hydrocarbon may also be substituted or condensed with other groups.

In the definitions of X, Y and R, the heterocyclic group is a cyclic group containing at least one heteroatom selected from O, S and N. The heterocyclic group is an aliphatic cyclic group or an aromatic cyclic group. The heterocyclic group is not specifically limited in carbon number. The heterocyclic group may have, for example, 2 to 40 carbon atoms. The heterocyclic group may contain a monocyclic or polycyclic moiety. Examples of the heterocyclic group include imidazol, thiazol, pyridyl, pyrimidyl, oxazol, etc. In this specification, it should be understood that, if a substituent which is bound to the benzene ring that is the core structure of chemical formula 1 is a heterocyclic group, the heterocyclic group may also be substituted or condensed with other groups.

In the definitions of X, Y and R, the reactive functional group is a group which can further react with other compounds. Specifically, the term "reactive functional group" refers to a group that can react with other compounds under reaction conditions known in the art. The kind of reactive functional group is not specifically limited, and examples thereof —OH, —SH, —NR$^a$R$^b$, etc., wherein R$^a$ and R$^b$ may each be hydrogen, alkyl, alkenyl, alkynyl, alkoxy, aryl, etc.

In the definitions of X, Y and R, the group convertible into a reactive functional group is a group which may further be substituted or replaced with the above-mentioned reactive functional groups. Specifically, the expression "group convertible into a reactive functional group" refers to a group which may be substituted or replaced with a group which can react with other compounds under reaction conditions known in the art. The kind of group convertible into a reactive functional group is not specifically limited, and examples thereof include an amine group, etc. Examples of the amine group include a —NH$_2$ group or an amine group having a substituent such as alkyl, aryl, etc.

According to one embodiment of the present invention, at least X of X, Y and R is a reactive functional group or a group convertible into a reactive functional group.

According to another embodiment of the present invention, at least X and Y of X, Y an R are either reactive functional groups or groups convertible into reactive functional groups.

According to one embodiment of the present invention, X and Y are either reactive functional groups or groups convertible into reactive functional and are in the meta or para position.

According to another embodiment of the present invention, X and Y are either reactive functional groups or groups convertible into reactive functional groups and are in the para position.

If X and Y are in the para position, the compound of chemical formula 1 may be represented by the following chemical formula 4:

[Chemical formula 4]

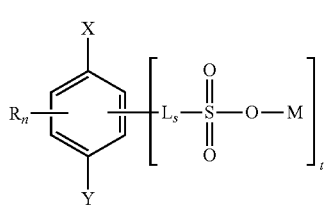

wherein,

X, Y, R, n, L, s, t and M are as defined in chemical formula 1.

According to one embodiment of the present invention, X and Y are reactive functional groups and are in the para position.

In the definition of L as above, the linking group comprising at least one fluorine atom is a divalent group which can connect the benzene ring with a sulfonate group (—SO$_3$—) and contains one or more fluorine atoms. "s" that represents the number of repeat units of L may not only be 1, but also be 2 or 3.

According to one embodiment of the present invention, L contains an alkylene group substituted with at least one fluorine atom.

According to one embodiment of the present invention, L comprises one or more alkylene groups substituted with at least one fluorine atom, and may further comprise an additional divalent group.

According to one embodiment of the present invention, L comprises an alkylene group having 1 to 10 carbon atoms and substituted with at least one fluorine atom. Herein, all the alkylene groups may be saturated with fluorine.

According to one embodiment of the present invention, chemical formula 1 is represented by the following chemical formula 5:

[Chemical formula 5]

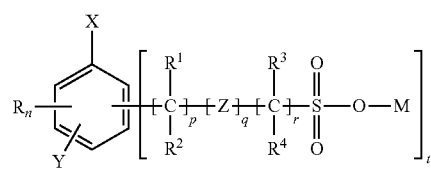

wherein,

X, Y, R, n, t and M are as defined in chemical formula 1, at least one of R$^1$ to R$^4$ is a fluorine atom, the other R$^1$ to R$^4$ groups other than fluorine are hydrogen, a C$_1$-C$_6$ alkyl or a C$_1$-C$_6$ alkyl substituted with fluorine; p is an integer ranging from 1 to 10, r is an integer ranging from 0 to 10, Z is a divalent group; and q is 0 or 1.

The R$^1$ to R$^4$, which are groups other than a fluorine atom, include, for example, hydrogen, —CH$_3$, —CF$_3$, etc.

Z is a divalent group, and the kind thereof is not specifically limited. For example, Z may be —O— or —S—.

According to one embodiment of the present invention, in chemical formula 5, p is an integer ranging from 1 to 5, q is 0 or 1, and r is an integer ranging from 0 to 5.

According to one embodiment of the present invention, in chemical formula 5, all of R$^1$ to R$^4$ may be fluorine.

M is an element of Group 1 on the Periodic Table. Examples of M include potassium (K), sodium (Na), hydrogen (H), etc.

According to one embodiment of the present invention, M is potassium (K) or sodium (Na). According to one embodiment of the present invention, if each of X and Y is a reactive functional group and if M is potassium (K) or sodium (Na), M can lower the reactivity of SO$_3^-$ by ionic bonding with SO$_3^-$ so that only X and Y of the compound of chemical formula 1 according to the present invention can react. In this case, M can be ion-exchanged with H through a post-treatment process later, if necessary.

The group

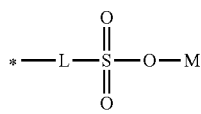

can be in the ortho-, meta- or para-position relative to X. According to one embodiment of the present invention, the group

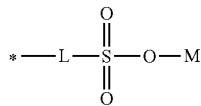

can be in the ortho-position relative to X. For example, when X and Y are in the para-position relative to each other, and the group

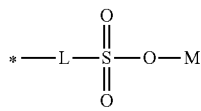

is in the ortho-position relative to X, the compound of chemical formula 1 can be represented by the following chemical formula 6:

[Chemical formula 6]

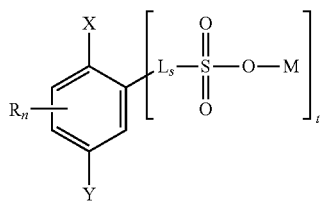

wherein,

X, Y, R, n, L, s, t and M are as defined in chemical formula 1.

Another embodiment of the present invention provides a method for preparing a compound of chemical formula 1, the method comprising the steps of:

a) preparing a compound of the following chemical formula 2;

[Chemical formula 2]

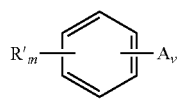

wherein,

R's are the same as or different from each other and are each hydrogen, an aliphatic hydrocarbon group, an aromatic hydrocarbon group, a heterocyclic group, a reactive functional group or a group convertible to a reactive functional group; m is an integer ranging from 1 to 5, and when m is 2 or more, R's may be the same as or different from each other and may together form an aliphatic or aromatic monocyclic or polycyclic ring, A is a halogen group; v is an integer ranging from 1 to 3, and when v is 2 or more, As are the same as or different from each other, and m+v is an integer ranging from 2 to 6;

b) preparing a compound of the following chemical formula 3;

[Chemical formula 3]

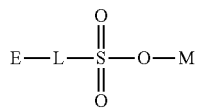

wherein,

L and M are as defined in chemical formula 1, and

E is a halogen group; and c) reacting the compound of chemical formula 2 with the compound of chemical formula 3 to obtain the compound of chemical formula 1.

R' in chemical formula 2 may not only be the same as X, Y or R of chemical formula 1, but also be a group convertible into X, Y or R. As used herein, the term "group convertible into" refers to a group which can be converted into X, Y or R under reaction conditions known in the art. R' is preferably a group which does not react under the reaction conditions of the steps a), b) and c) as described above.

In one embodiment of the present invention, at least one of R's may be a group convertible into a reactive functional group. In this case, the method for preparing the compound of chemical formula 1 may further comprise, after the step c), the step of d) converting at least one of the R' groups into a reactive functional group. For example, the R' group is an —OAc group that may be converted into an —OH group by the step d).

The method for preparing the compound of chemical formula 1 according to one embodiment of the present invention may further comprise, before the step b), the step of preparing the compound of chemical formula 3 using a compound of the following chemical formula 7:

[Chemical formula 7]

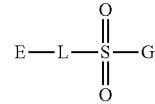

wherein,

L and M are as defined in chemical formula 1, and each of E and G is a halogen group.

In the definitions of A, E and G, the halogen group may be fluorine, chlorine, bromine, iodine, etc. In a preparation example as described below, a compound wherein A is bromine, E is iodine, and G is fluorine is used, but is not limited thereto. The kind of A, E and G may vary according to the reaction order or conditions. For example, when the compound of chemical formula 7 is first converted into the compound of chemical formula 3 comprising —$SO_3M$, there may be used a compound wherein E is iodine and a compound wherein A is bromine or iodine. However, E and G may be different halogen groups so as to react under different reaction conditions. However, they are not limited thereto and may be controlled according to the reaction order or conditions.

Hereinafter, the method for preparing the compound of chemical formula 1 will be exemplified based on specific compounds. A person skilled in the art can prepare compounds falling within the scope of chemical formula 1 by changing the kind or position of substituents in starting materials, based on the examples described below. In addition, the reaction conditions as described below may be controlled according to the kind of starting material or intermediate.

In a specific example, the compound of chemical formula 1 can be prepared by the following method comprising five steps.

<Step 1>

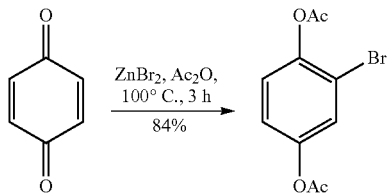 [SMILES: O=C1C=CC(=O)C=C1 ; CC(=O)Oc1ccc(OC(C)=O)c(Br)c1]

In step 1, 1,4-benzoquinone was reacted under the presence of $ZnBr_2$ and $Ac_2O$ at 100° C. for 3 hours. The reaction conditions such as the reaction time or temperature may be controlled according to the kind of substituent in the compound. In this example, 1,4-benzoquinone was as the starting material, but the position of the substituent can be changed either by using a compound having ketone at a different position in benzoquinone or by controlling the substitution position of bromine in the compound obtained in step 1. In addition, the kind of substituent may be changed by replacing either the substituent group of the starting material or the materials used during the reaction, for example, $ZnBr_2$ and $Ac_2O$, with other materials. Herein, 84% is the conversion rate or yield.

<Step 2>

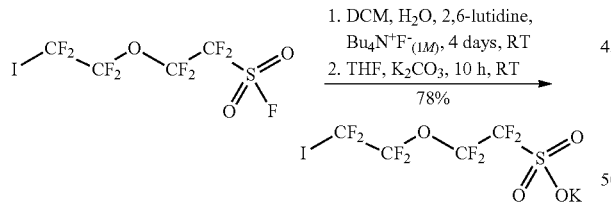

Step 2 may be carried out in any order in relation to step 1. In step 2, there was used a starting material in which iodine and fluorine groups were bound to both ends of a compound comprising —$(CF_2)_2$—O—$(CF_2)_2$— and —$SO_2$— groups as the linking group L, respectively. First, the starting material was reacted under the presence of dichloromethane (DCM), $H_2O$, 2,6-lutidine and $Bu_4N^+F^-$ (1M) at room temperature for 4 days. Then, it was reacted under the presence of tetrahydrofuran (THF) and $K_2CO_3$ at room temperature for 10 hours. The reaction conditions such as reaction time or reaction temperature may be controlled according to the kind of substituents in the compound.

In this example, the starting material having the —$(CF_2)_2$—O—$(CF_2)_2$— group as the linking group L was used, but a compound having a different kind of linking group L may be prepared by changing the kind of linking group L in the starting material. In addition, the starting material used was the compound comprising iodine (I) and fluorine (F) groups bound to both ends, respectively, but the halogen groups may be replaced with other halogen groups depending on the reaction conditions. However, the halogen groups at both ends of the starting material are preferably different from each other so that they can react under different conditions. Herein, 78% is the conversion rate or yield.

<Step 3>

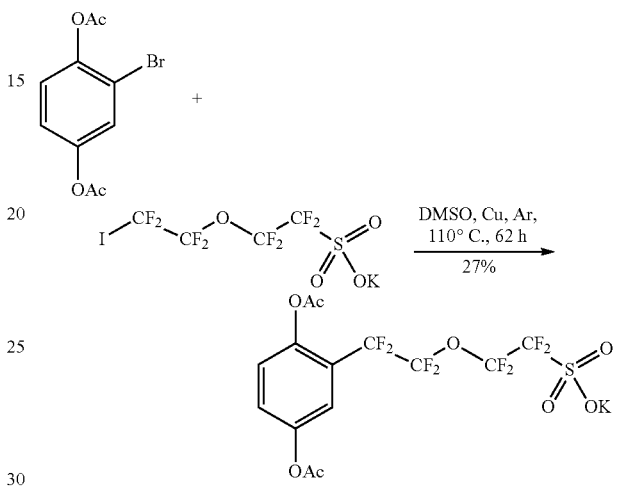

In step 3, the reaction product obtained in step 1 and the reaction product obtained in step 2 were reacted under the presence of dimethyl sulfoxide (DMSO) and Cu under an Ar atmosphere at 110° C. for 62 hours. The reaction conditions such as the reaction time, reaction temperature, etc. may be controlled according to the kind of substituents in the compound. Herein, 27% is the conversion rate or yield.

<Steps 4 and 5>

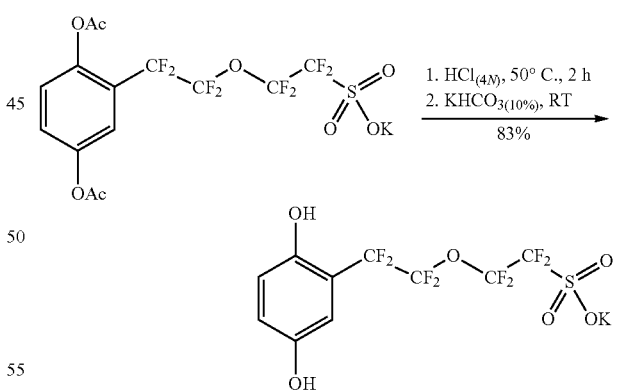

In step 4, 4N (normal concentration) HCl was added to the compound of step 3 and reacted at 50° C. for 2 hours. Then, in step 5, a compound having —OH groups as reactive functional groups was prepared by adding 10 wt % $KHCO_3$ aqueous solution to the compound of step 4 and reacting the mixture at room temperature. The reaction conditions such as reaction time, reaction temperature, etc. may be controlled according to the kind of substituent in the compound. In this example, the compound having an —OH group as a reactive functional group was prepared, but the substituent of the final compound may be controlled by changing the kind of substituent of the starting material or the material added during the reaction. Herein, 83% is the conversion rate or yield.

The compound according to the present invention can be used not only as various materials per se, but also as a raw material for preparing other materials.

Another embodiment of the present invention provides a polymer electrolyte membrane comprising the compound of chemical formula 1.

Since a conventional fluorine-based electrolyte membrane among electrolyte membranes for fuel cells is expensive, there have been attempts to develop a hydrocarbon-based electrolyte membrane which is relatively inexpensive. The electrolyte membrane may be a block polymer, because phase separation into hydrophilic and hydrophobic domains is important. However, in the case of a hydrocarbon-based block polymer, phase separation is difficult when the distance between the main chain and the sulfone group is short. However, the compound of chemical formula 1 can provide an electrolyte membrane having improved phase separation properties, since it contains a linking group containing fluorine between an aromatic phenyl group and a sulfone group, especially an aliphatic group containing fluorine.

The compound of chemical formula 1 may be used either as a monomer for preparing a polymer forming an electrolyte membrane or an additive to the polymer.

When the compound of chemical formula 1 is used as a monomer for preparing a polymer, the polymer comprising the compound of chemical formula 1 may be a homopolymer of the compound of chemical formula 1, and may comprise an additional comonomer. The additional comonomer may be one known in the art. In this case, one or more comonomers may be used.

Examples of the comonomer that may be used in the present invention include monomers constituting a perfluorosulfonic acid polymer, a hydrocarbon-based polymer, polyimide, polyvinylidenfluoride, polyethersulphone, polyphenylenesulphide, polyphenylene oxide, polyphosphazine, polyethylene naphthalate, polyester, doped polybenzimidazole, polyetherketone, polysulfone, or acids or bases thereof.

The above polymer may further comprise, in addition to the compound of chemical formula 1, a sulfonate-based compound.

In a specific embodiment, the polymer may be a polymer comprising, in addition to the compound of chemical formula 1, 4,4-difluorobenzophenone and 3,5-bis(4-fluorobenzoyl)phenyl(4-fluorophenyl)methanone. In addition, the polymer may further comprise a sulfonate-based compound such as a hydroquinone sulfonic acid potassium salt.

In another embodiment, the polymer may be a multi-block copolymer obtained by adding 4,4'-difluorobenzophenone, 9,9-bis(hydroxyphenyl)fluorine and 3,5-bis(4-fluorobenzoyl)phenyl(4-fluorophenyl)-methanone to a hydrophilic oligomer of 4,4'-difluorobenzophenone and 3,5-bis(4-fluorobenzoyl)phenyl(4-fluorophenyl)methanone are polymerized, and then reacting the mixture with the compound of chemical formula 1.

When the polymer comprises a comonomer in addition to the compound of chemical formula 1, the content of the additional comonomer in the polymer may be, for example, greater than 0 wt % but not greater than 95 wt %.

The contents of the compound of chemical formula 1 and the additional comonomer in the polymer may be controlled according to a proper ion exchange capacity (IEC) value needed for the fuel cell electrolyte membrane to be applied. When a polymer for preparing a fuel cell separator is synthesized, the polymer may be designed by calculating the value of ion exchange capacity (IEC) meq./g=mmol/g. The content of the monomer in the polymer may be selected within the range of $0.5 \leq IEC \leq 3$ depending on requirements. The compound of chemical formula 1 may be used to design an electrolyte membrane having a low IEC value while showing the same ion conductivity value as those of conventional electrolyte membranes.

A polymer comprising the compound of chemical formula 1 may have a weight-average molecular weight of tens of thousands to millions. Specifically, the weight-average molecular weight of the polymer may be selected within the range of 100,000 to 1,000,000.

The polymer comprising the compound of chemical formula 1 is preferably a block copolymer. The polymer comprising the compound of chemical formula 1 may be synthesized by a polycondensation process in which the compound of chemical formula 1 reacts with a halogen-containing monomer so that the OH group of the compound of chemical formula 1 reacts with a halogen element such as F or Cl to form HF or HCl.

When a polymer electrolyte membrane is prepared using a polymer comprising the compound of chemical formula 1, the polymer electrolyte membrane can be prepared by adding a solvent to the polymer to make a polymer solution, and then forming the polymer solution into a film using a solvent casting method. If necessary, the $SO_3M$ group can be converted into an $SO_3H$ group by acid treatment.

When the compound of chemical formula 1 is added as additive to the polymer electrolyte membrane, the content of the compound of chemical formula in the electrolyte membrane is not specifically limited, but, may be, for example, greater than 0 wt % but not greater than 95 wt %.

When the compound of chemical formula 1 is added as an additive to the polymer electrolyte membrane, the polymer electrolyte membrane can further comprise one or more polymers selected from among a perfluorosulfonic acid polymer, a hydrocarbon-based polymer, polyimide, polyvinylidene fluoride, polyethersulphone, polyphenylenesulphide, polyphenyleneoxide, polyphosphazene, polyethylene naphthalate, polyester, doped polybenzimidazole, polyetherketone, polysulfone, and acids or bases thereof.

According to one embodiment of the present invention, the ion conductivity and ion exchange capacity (IEC) of the polymer electrolyte membrane may be appropriately selected depending on not only the intended use of a fuel cell to which it is applied, but also a material added to the polymer electrolyte membrane, for example, the kind of monomer or additive contained in the polymer. For example, when the polymer electrolyte membrane is applied to a fuel cell, it may be designed to have $0.5 \leq IEC \leq 3$ and $0.5 \leq IEC \leq 2.5$, but the scope of the present invention is not limited thereto, and suitable ion conductivity and ion exchange capacity values may be selected as required. The polymer electrolyte membrane according to the present invention has low IEC value while showing ion conductivity value equal to or higher than that of a conventional polymer electrolyte membrane.

The polymer electrolyte membrane according to the present invention can be prepared using the same material or method used in the art, except that the compound of chemical formula 1 is used.

For example, the polymer electrolyte membrane may be prepared to have a thickness ranging from several microns to several hundred microns.

The present invention provides a membrane electrode assembly comprising: an anode electrode; a cathode electrode; and a polymer electrolyte membrane interposed between the anode electrode and the cathode electrode and comprising the compound of chemical formula 1.

The anode electrode may comprise an anode catalyst layer and an anode gas diffusion layer. The anode gas diffusion layer may comprise an anode micro-porous layer and an anode electrode substrate.

The cathode electrode may comprise a cathode catalyst layer and a cathode gas diffusion layer. The cathode gas diffusion layer may comprise a cathode micro-porous layer and a cathode electrode substrate.

FIG. 1 schematically depicts the principle by which electricity is generated in a fuel cell. The most fundamental unit for generating electricity is a membrane electrode assembly (MEA) which comprises an electrolyte membrane (M) and the anode (A) and cathode (C) electrodes formed on both sides of the electrolyte membrane (M). Referring to FIG. 1 showing the principle of electricity generation in a fuel cell, in the anode (A) electrode, the oxidation of a fuel (F) comprising hydrogen or a hydrocarbon such as methanol or butane occurs to thereby generate hydrogen ions ($H^+$) and electrons ($e^-$), and subsequently the hydrogen ions move to the cathode (C) electrode through the electrolyte membrane (M). In the cathode (C) electrode, the hydrogen ions transferred through the electrolyte membrane (M) react with an oxidant (O) such as oxygen and electrons to produce water (W). This reaction causes the movement of electrons to an external circuit.

Figure 2:
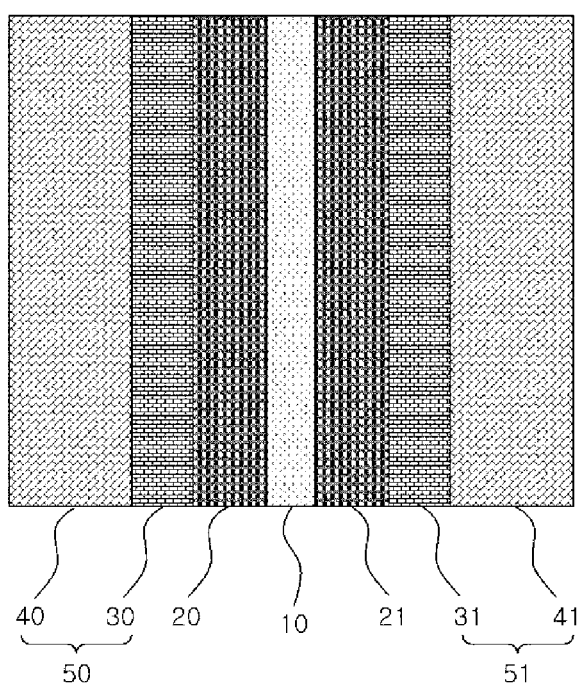
FIG. 2 is a schematic drawing showing the structure of a membrane electrode assembly for the fuel cell.

FIG. 2 schematically depicts the structure of a membrane electrode assembly for a fuel cell. As shown therein, the membrane electrode assembly for the fuel cell comprises an electrolyte membrane 10, and an anode electrode and a cathode electrode, which are placed opposite to each other with the electrolyte membrane 10 interposed therebetween.

The anode electrode comprises an anode catalyst layer 20 and an anode gas diffusion layer 50, wherein the anode gas diffusion layer 50 comprises an anode micro-porous layer 30 and an anode electrode substrate 40. Herein, the anode gas diffusion layer is interposed between the anode catalyst layer and the electrolyte membrane.

The cathode electrode comprises a cathode catalyst layer 21 and a cathode gas diffusion layer 51, wherein the cathode gas diffusion layer 51 comprises a cathode micro-porous layer 31 and a cathode electrode substrate 41. Herein, the cathode gas diffusion layer is interposed between the cathode catalyst layer and the electrolyte membrane.

The catalyst layer of the anode electrode, on which the oxidation of the fuel occurs, may preferably comprise a catalyst selected from the group consisting of platinum, ruthenium, osmium, a platinum-ruthenium alloy, a platinum-osmium alloy, a platinum-paladium alloy and a platinum-transition metal alloy. The catalyst layer of the cathode electrode, on which the reduction of the oxidant occurs, may preferably comprise a catalyst of platinum or a platinum-transition metal alloy. The catalysts may be used per se or supported on a carbon-based carrier.

A process for introducing the catalyst layer may be performed by a conventional method known in the art. For example, the catalyst layer may be formed by coating a catalyst ink directly on the electrolyte membrane or by coating the catalyst ink on the gas diffusion layer. Herein, the method for coating the catalyst ink is not specifically limited, but a spray coating, tape casting, screen printing, blade coating, die coating or spin coating method may be used. The catalyst ink may typically comprise a catalyst, a polymer ionomer and a solvent.

The gas diffusion layer not only serves as a current conductor but also as a channel for reactant gas and water and has a porous structure. Therefore, the gas diffusion layer may comprise a conductive substrate. Preferably, the conductive substrate may be made of carbon paper, carbon cloth or carbon felt. The gas diffusion layer may further comprise a micro-porous layer between the catalyst layer and the conductive substrate. The micro-porous layer may be used to improve the performance of the fuel cell under low humidity conditions, and serves to reduce the leakage of water from the gas diffusion layer so that the electrolyte membrane is in a sufficiently wet state.

Another embodiment of the present invention provides a fuel cell comprising:
a stack comprising two or more membrane electrode assemblies according to the present invention and a separator interposed between the membrane electrode assemblies;
a fuel supply unit for supplying fuel to the stack; and
an oxidant supply unit for supplying an oxidant to the stack.

Figure 3:
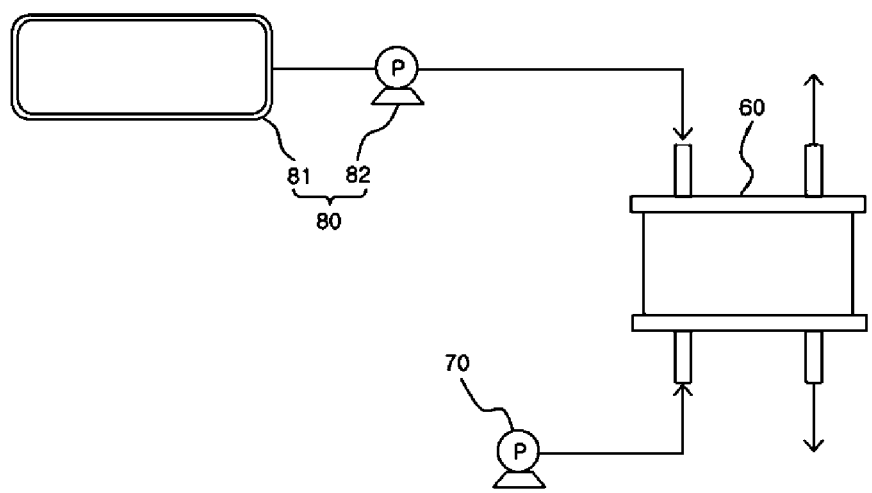
FIG. 3 is a schematic drawing showing one example of a fuel cell.

FIG. 3 schematically depicts the structure of a fuel cell. As shown therein, the fuel cell comprises a stack 60, an oxidant supply unit 70 and a fuel supply unit 80.

The stack 60 comprises one more membrane electrode assemblies as described above, and when it comprises two or more membrane electrode assemblies, it comprises a separator interposed between membrane electrode assemblies. The separator functions to prevent the membrane electrode assemblies from being electrically connected to each other and to transfer the externally supplied fuel and oxidant to the membrane electrode assembly.

The oxidant supply unit 70 functions to supply the oxidant to the stack 60. Oxygen is typically used as the oxidant, and oxygen or air injected by means of a pump 70 may be used as the oxidant.

The fuel supply unit 80 functions to supply fuel to the stack 60 and may comprise a fuel tank 81 for storing the fuel and a pump 82 for supplying the fuel stored in the fuel tank 81 to the stack 60. Gaseous or liquid hydrogen or a hydrocarbon fuel may be used as the fuel. Examples of hydrocarbon fuel include methanol, ethanol, propanol, buthanol or natural gas.

The compound according to the present invention can be used either as various materials per se or as a raw material for preparing other materials.

Hereinafter, the present invention will be described in further detail with reference to examples. However, these examples are for illustrative purposes and are not intended to limit the scope of the present invention.

Preparation Example

Method for synthesis of 1,1,2,2-tetrafluoro-(1,1,2,2-tetrafluro-(2,5-dihydroxyphenyl)ethoxy)ethanesulfonate of potassium (also known as 5-(2,5-dihydroxyphenyl)octafluoro-3-oxapentanesulfonate of potassium)

1. 2-bromohydroquinone Diacetate [1] (Compound I)

1,4-benzoquinone (0.052 mol, 5.65 g) was added to a suspension of anhydrous zinc bromide (0.065 mol, 14.7 g) in 15 ml of anhydrous acetic acid with stirring. The mixture was maintained at 100° C. for 3 hours, and then cooled to room temperature and poured into 40 ml of water. The precipitate was filtered, washed with water (20 ml, 3 times), and recrystallized from a water-ethanol mixture (50% of ethanol). The yield of the product was 84%. The melting point was 76° C. to 77° C. $^1$H NMR (300 MHz, DMSO-$d_6$), δ: 2.27 (s, 3H); 2.33 (s, 3H); 7.23 (dd, J=2.4, 8.7, 1H); 7.34 (d, J=8.7, 1H); 7.59 (d, J=2.4, 1H).

2. 1,1,2,2-Tetrafluoro-2-(1,1,2,2-tetrafluoro-2-iodineethoxy)ethanesulfonate of Potassium [2] (Compound II)

To a solution of 1,1,2,2-tetrafluoro-2-(1,1,2,2-tetrafluoro-2-iodinethoxy)ethanesulfofluoride (0.268 mol, 114 g) in 40 g of methylene chloride, 38 ml of water, 2,6-lutidine (0.34 mol, 40 ml) and 0.8 ml of 1M solution of tetrabutylammonium fluoride in THF were added. The reaction mixture was stirred at room temperature for 4 days, and then extracted with methylene chloride (200 ml, 3 times). The extract was dried over $Na_2SO_4$ and dissolved in 80 ml of THF. Potassium carbonate (0.155 mol, 21.4 g) was added to the solution, and then the mixture was stirred at room temperature for 10 hours. An excess amount of potassium carbonate was removed by filtration, and then the solvent was evaporated under reduced pressure. The resulting solid compound was recrystallized from a 1:1 mixture of THF:toluene. The yield of the product was 96.2 g (78%).

3. 1,1,2,2-Tetrafluoro-2-(1,1,2,2-tetrafluoro-(2,5-diacetoxyphenyl)ethoxy)ethanesulfonate of Potassium (Compound III)

Copper powder (0.71 ml, 45.5 g) was placed in a reaction flask, heated to 150° C. in an argon atmosphere, maintained under such conditions for 5 minutes and then cooled to room temperature. Subsequently, compound I (0.143 mol, 39 g), compound II (0.171 mol, 79 g) and 130 ml of dimethylsulphoxide (DMSO) were added thereto in an inert atmosphere. After sealing the flask, the reaction mixture was stirred under an argon atmosphere at 110° C. for 62 hours. The mixture was cooled to room temperature, dissolved in 200 ml of isopropyl alcohol and excess amounts of the catalyst and inorganic material were removed using zeolite. Isopropyl alcohol was removed using a rotary evaporator. 300 ml of ethyl acetate was added to the remaining compound, after which the organic layer was washed with a saturated solution of potassium chloride, and then dried over $Na_2SO_4$. The remaining solvent was removed under reduced pressure. The resulting oil was treated with toluene, and impurities were removed from the oil by decantation using diethyl ether. The resulting light beige material was washed with an additional amount of ester on a filter. The yield of the product was 19 g (27%). The melting point was 170° C. to 173° C. $^1$H NMR (300 MHz, DMSO-$d_6$), δ: 2.27 (s, 3H); 2.29 (s, 3H); 7.42 (dd, J=2.4, 8.7, 1H); 7.50 (d, J=8.7, 1H); 7.52 (d, J=8.7, 1H). [M-K]$^-$: calculated—488.9885; experimental value—488.9863.

4. 1,1,2,2-Tetrafluoro-2-(1,1,2,2-tetrafluoro-(2,5-dihydroxyphenyl)ethoxy)ethanesulfonic Acid (Compound IV)

Compound III (0.025 mol, 13 g) was dissolved in 650 ml of acetone. 650 ml of 4N HCl solution was added to the above solution, and then the mixture was stirred at 50° C. for 2 hours. The solvent was removed using a rotary evaporator while adding water twice to the mixture, thereby securing the complete removal of acetic acid. The resulting product was 9.1 g of oil (90%). $^1$H NMR (300 MHz, DMSO-$d_6$), δ: 6.75 (narrow d, 1H); 6.82 (m, H); 9.46 (broad. S, 1H).

5. 1,1,2,2-tetrafluoro-2-(1,1,2,2-tetrafluoro-(2,5-dihydroxyphenyl)ethoxy)ethanesulfonate of Potassium (Compound V)

22.5 ml of a 10% solution of potassium hydrocarbonate in water was added to compound IV. The mixture was maintained at room temperature for 20 minutes, and then the solvent was evaporated under reduced pressure. 50 ml of acetone was added three times during the evaporation to completely remove water. The resulting product was oil, which was then dried at 1 mm Hg for 2 hours, followed by solidification. Yield: 9.16 g (92%). $^1$H NMR (300 MHz, DMSO-$d_6$), δ: 6.75 (narrow d, 1H); 6.82 (m, H); 9.13 (s, 1H); 9.46 (s, 1H). [M-K]$^-$: calculated—404.9567; experimental value—404.9545.

Experimental Example

1. Polymer Synthesis

A compound (57.96 g) prepared in the above preparation example, 4,4'-difluorobenzophenone (23.40 g) and 3,5-bis(4-fluorobenzoyl)phenyl(4-fluorophenyl)methanone (0.98 g) were placed into a round-bottom flask equipped with a Dean-Stark trap and a condenser, and were allowed to react in 150 ml of dimethyl sulfoxide (DMSO) and 200 ml of benzene in the presence of 29.03 g of $K_2CO_3$ as a catalyst in a nitrogen atmosphere (synthesis of hydrophilic oligomer).

The above reaction mixture was stirred at 140° C. in an oil bath for 4 hours so that benzene flowed backward while the azeotropic mixture was removed by adsorption onto the molecular sieve of the Dean-Stark device. Then, the reaction mixture was heated to 180° C. and polycondensed for 20 hours. After completion of the reaction, the temperature of the reaction solution was decreased to 60° C., and then 4,4'-difluorobenzophenone (5.49 g), 9,9-bis(hydroxyphenyl)fluorine (11.04 g) and 3,5-bis(4-fluorobenzoyl)phenyl(4-fluorophenyl)-methanone (0.24 g) was placed in the same flask, and the mixture was allowed to react in 100 ml of DMSO and 200 ml of benzene in a nitrogen atmosphere in the presence of $K_2CO_3$ (8.71 g) as the catalyst.

The reaction mixture was stirred again at a temperature of 140° C. in an oil bath for 4 hours so that benzene flowed backward while the azeotropic mixture was removed by adsorption onto the molecular sieve of the Dean-Stark device. Then, the reaction mixture was heated to 180° C. and polycondensed for 20 hours. Afterward, the temperature of the reaction product was decreased to room temperature, and the product was diluted by additionally adding DMSO. The diluted product was poured into an excess amount of methanol, and the copolymer was separated from the solvent.

Then, an excess amount of potassium carbonate was removed using water, and the residue was filtered. The resulting copolymer was dried in a vacuum oven at 80° C. for 12 hours or more, thereby preparing a branched sulfonated multi-block copolymer comprising a hydrophobic block and a hydrophilic block, which are alternately linked by a chemical bond.

2. Film Casting

The above-synthesized multi-block copolymer was dissolved in dimethyl sulfoxide (DMSO) to prepare a 5-10 wt % solution of the polymer. The polymer solution was cast on a substrate over the horizontal plate of an applicator in a clean bench set at 40° C. by using a Doctor blade, thereby forming a polymer film. The polymer film was soft-baked for 2 hours, after which it was placed in an oven set at 100° C. and was dried for 1 day, thereby preparing a polymer electrolyte membrane containing the hydrophilic carbon-based material.

The polymer electrolyte membrane prepared as described above had an IEC value of 1.2-1.6 and the hydrogen ion conductivity thereof was 2.5E-0.2 at room temperature, 3.1E-

02 at 40° C., 4.2E-02 at 60° C., 5.2E-02 at 80° C., and 6.8E-02 at 100° C. In summary, the polymer electrolyte membrane prepared as described above has a low IEC value and high hydrogen ion conductivity, and thus can be effectively used as a polymer electrolyte membrane for a fuel cell. When such a polymer electrolyte membrane is applied to a fuel cell, the performance of the fuel cell can be greatly improved.

DESCRIPTION OF REFERENCE NUMERALS USED IN THE DRAWINGS

10: electrolyte membrane
20, 21: catalyst layer
30, 31: micro-porous layer
40, 41: electrode substrate
50, 51: gas diffusion layer
60: stack
70: oxidant supply unit
80: fuel supply unit
81: fuel tank
82: pump

The invention claimed is:

1. A compound of the following chemical formula 5:

[Chemical formula 5]

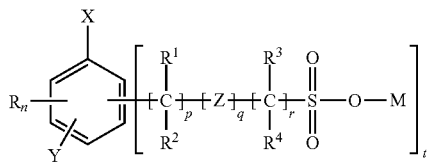

wherein,

X, Y and R are each independently hydrogen, an aliphatic hydrocarbon group, an aromatic hydrocarbon group, a heterocyclic group, OH, —SH, or —OAc, n is an integer ranging from 1 to 3, and when n is 2 or more, Rs may be the same as or different from each other and may together form an aliphatic or aromatic monocyclic or polycyclic ring, M is an element of Group 1 of the Periodic Table, t is an integer ranging from 1 to 3, and when t is 2 or more, the substituents in the parenthesis are the same as or different from each other, and n+t is an integer ranging from 2 to 4, at least one of $R^1$ to $R^4$ is a fluorine atom, and $R^1$ to $R^4$ that are not fluorine atoms are hydrogen, a $C_1$-$C_6$ alkyl or a $C_1$-$C_6$ alkyl substituted with fluorine, p is an integer ranging from 1 to 10, and r is an integer ranging from 0 to 10, and Z is a divalent group, and q is 0 or 1.

2. The compound of claim 1, wherein at least X and Y of X, Y and R are each independently —OH, —SH, or —OAc, wherein each of $R^a$ and $R^b$ is hydrogen, alkyl, alkenyl, alkynyl, alkoxy or aryl.

3. The compound of claim 1, wherein p is an integer ranging from 1 to 5, and r is an integer ranging from 0 to 5.

4. The compound of claim 1, wherein all of $R^1$ to $R^4$ are fluorine.

5. The compound of claim 1, wherein M is potassium (K), sodium (Na) or hydrogen (H).

6. A polymer electrolyte membrane comprising a compound according claim 1.

7. The polymer electrolyte membrane of claim 6, wherein the polymer electrolyte membrane comprises a polymer comprising the compound of chemical formula 1.

8. The polymer electrolyte membrane of claim 6, wherein the polymer electrolyte membrane further comprises one or more polymers selected from among a perfluorosulfonic acid polymer, a hydrocarbon-based polymer, polyimide, polyvinylidene fluoride, polyethersulfone, polyphenylene sulphide, polyphenylene oxide, polyphosphazene, polyethylene naphthalate, polyester, doped polybenzimidazole, polyetherketone, polysulfone, and acids or bases thereof.

9. A membrane electrode assembly comprising: an anode electrode; a cathode electrode; and a polymer electrolyte membrane according to claim 6, interposed between the anode electrode and the cathode electrode.

10. The membrane electrode assembly of claim 9, wherein the anode electrode comprises an anode catalyst layer and an anode gas diffusion layer, and the cathode electrode comprises a cathode catalyst layer and a cathode gas diffusion layer.

11. A fuel cell comprising:

a stack comprising two or more membrane electrode assemblies according to claim 9 and a separator interposed between the membrane electrode assemblies;

a fuel supply unit for supplying fuel to the stack; and an oxidant supply unit for supplying an oxidant to the stack.

* * * * *